(12) United States Patent
Tirtowidjojo et al.

(10) Patent No.: US 10,065,157 B2
(45) Date of Patent: Sep. 4, 2018

(54) MIXER AND PROCESSES INCORPORATING THE SAME

(71) Applicant: Blue Cube IP LLC, Midland, MI (US)

(72) Inventors: Max M. Tirtowidjojo, Lake Jackson, TX (US); Hua Bai, Lake Jackson, TX (US); Edward M. Calverley, Midland, MI (US)

(73) Assignee: Blue Cube IP LLC, Clayton, MO (US)

( * ) Notice: Subject to any disclaimer, the term of this patent is extended or adjusted under 35 U.S.C. 154(b) by 393 days.

(21) Appl. No.: 14/436,604

(22) PCT Filed: Oct. 14, 2013

(86) PCT No.: PCT/US2013/064825
§ 371 (c)(1),
(2) Date: Apr. 17, 2015

(87) PCT Pub. No.: WO2014/066083
PCT Pub. Date: May 1, 2014

(65) Prior Publication Data
US 2016/0158715 A1   Jun. 9, 2016

Related U.S. Application Data

(60) Provisional application No. 61/718,920, filed on Oct. 26, 2012.

(51) Int. Cl.
*B01J 19/24* (2006.01)
*C07C 17/04* (2006.01)
(Continued)

(52) U.S. Cl.
CPC .......... *B01F 5/0653* (2013.01); *B01F 5/0652* (2013.01); *B01J 4/002* (2013.01);
(Continued)

(58) Field of Classification Search
CPC ....... B01F 5/0653; B01F 5/0652; B01J 19/24; B01J 4/002; C07C 17/04
(Continued)

(56) References Cited

U.S. PATENT DOCUMENTS 1,504,443 A   8/1924   Gibbons
2,119,484 A   5/1938   Levine et al.
(Continued)

FOREIGN PATENT DOCUMENTS

CH   609022      6/1974
CN   101215220   7/2008
(Continued)

OTHER PUBLICATIONS

Michigan Technological Univ., "Free-Radical Chlorination with Sulfuryl Chloride", Nov. 15, 2001, 1-7.
(Continued)

*Primary Examiner* — Huy Tram Nguyen
(74) *Attorney, Agent, or Firm* — Polsinelli PC

(57) ABSTRACT

The present invention relates to a mixer, an apparatus comprising the mixer and a reactor, and processes incorporating the same. The mixer comprises an inlet (104) to a chamber (102), wherein the chamber inlet angle is less than 90°. The mixer further comprises an expander zone (106) that expands outwardly at an expander angle of less than 90°. The mixer may be coupled to a reactor at its outlet, which may closely approximate the size of the reactor inlet due to the expander (106).

11 Claims, 5 Drawing Sheets

(51) Int. Cl.
*B01F 5/06* (2006.01)
*B01J 4/00* (2006.01)
*B01F 5/00* (2006.01)

(52) U.S. Cl.
CPC .............. *B01J 19/24* (2013.01); *C07C 17/04* (2013.01); *B01F 5/0062* (2013.01); *B01J 2219/1943* (2013.01); *B01J 2219/24* (2013.01)

(58) Field of Classification Search
USPC ....................................................... 422/224
See application file for complete search history.

(56) References Cited

U.S. PATENT DOCUMENTS

| | | |
|---|---|---|
| 2,179,378 A | 11/1939 | Metzger |
| 2,207,193 A | 7/1940 | Groll |
| 2,299,441 A | 10/1942 | Vaughan et al. |
| 2,302,228 A | 11/1942 | Kharasch et al. |
| 2,370,342 A | 2/1945 | Zellner |
| 2,378,859 A | 6/1945 | Martin |
| 2,379,551 A * | 7/1945 | Talley ................... B01F 5/0415 417/196 |
| 2,435,983 A | 2/1948 | Schmerling |
| 2,449,286 A | 9/1948 | Fairbairn |
| 2,588,867 A | 3/1952 | Morris |
| 2,630,461 A | 3/1953 | Sachsse et al. |
| 2,688,592 A | 9/1954 | Skeeters |
| 2,762,611 A | 9/1956 | Monroe |
| 2,765,359 A | 10/1956 | Pichler et al. |
| 2,964,579 A | 12/1960 | Weller et al. |
| 2,973,393 A | 2/1961 | Monroe |
| 3,000,980 A | 9/1961 | Asadorian |
| 3,094,567 A | 6/1963 | Eaker |
| 3,112,988 A | 12/1963 | Coldren et al. |
| 3,444,263 A | 5/1969 | Fernald |
| 3,446,859 A | 5/1969 | Weil |
| 3,502,734 A | 3/1970 | Baird |
| 3,525,595 A | 8/1970 | Zirngibl et al. |
| 3,551,512 A | 12/1970 | Loeffler |
| 3,558,438 A | 1/1971 | Schoenbeck |
| 3,615,202 A * | 10/1971 | Stern ...................... C01G 23/07 106/442 |
| 3,651,019 A | 3/1972 | Asscher |
| 3,676,508 A | 7/1972 | Krekeler |
| 3,819,731 A | 6/1974 | Pitt |
| 3,823,195 A | 7/1974 | Smith |
| 3,872,664 A | 3/1975 | Lohmann |
| 3,914,167 A | 10/1975 | Ivy |
| 3,920,757 A | 11/1975 | Watson |
| 3,926,758 A | 12/1975 | Smith |
| 3,948,858 A | 4/1976 | Weirsum |
| 3,954,410 A | 5/1976 | Pohl et al. |
| 4,038,372 A | 7/1977 | Colli |
| 4,043,766 A * | 8/1977 | Gernhardt .................. C10J 3/57 239/433 |
| 4,046,656 A | 9/1977 | Davis et al. |
| 4,051,182 A | 9/1977 | Pitt |
| 4,145,187 A * | 3/1979 | Oliver .................... B01D 47/06 110/261 |
| 4,319,062 A | 3/1982 | Boozalis et al. |
| 4,381,187 A * | 4/1983 | Sederquist ............... B01J 19/26 252/373 |
| 4,513,154 A | 4/1985 | Kurtz |
| 4,535,194 A | 8/1985 | Woodard |
| 4,550,752 A * | 11/1985 | Manders ............ D03D 47/3013 139/435.4 |
| 4,614,572 A | 9/1986 | Holbrook |
| 4,644,907 A | 2/1987 | Hunter |
| 4,650,914 A | 3/1987 | Woodard |
| 4,661,648 A | 4/1987 | Franklin |
| 4,702,809 A | 10/1987 | Mueller |
| 4,714,792 A | 12/1987 | Mueller et al. |
| 4,716,255 A | 12/1987 | Mueller |
| 4,726,686 A | 2/1988 | Wolf |
| 4,727,181 A | 2/1988 | Kruper |
| 4,849,554 A | 7/1989 | Cresswell et al. |
| 4,894,205 A | 1/1990 | Westerman |
| 4,902,393 A | 2/1990 | Mueller |
| 4,999,102 A | 3/1991 | Cox |
| 5,057,634 A | 10/1991 | Webster |
| 5,132,473 A | 7/1992 | Furutaka |
| 5,171,899 A | 12/1992 | Furutaka |
| 5,178,844 A | 1/1993 | Carter et al. |
| 5,246,903 A | 9/1993 | Harley |
| 5,254,771 A | 10/1993 | Cremer |
| 5,254,772 A | 10/1993 | Dukat |
| 5,254,788 A | 10/1993 | Gartside |
| 5,262,575 A | 11/1993 | Dianis |
| 5,315,044 A | 5/1994 | Furutaka |
| 5,367,105 A | 11/1994 | Miyazaki et al. |
| 5,414,166 A | 5/1995 | Kim |
| 5,504,266 A | 4/1996 | Tirtowidjojo et al. |
| 5,684,219 A | 11/1997 | Boyce |
| 5,689,020 A | 11/1997 | Boyce |
| 5,811,605 A | 9/1998 | Tang |
| 5,895,825 A | 4/1999 | Elsheikh |
| 5,986,151 A | 11/1999 | Van Der Puy |
| 6,111,150 A | 8/2000 | Sakyu |
| 6,118,018 A | 9/2000 | Savidakis |
| 6,160,187 A | 12/2000 | Strickler |
| 6,187,976 B1 | 2/2001 | Van Der Puy |
| 6,229,057 B1 | 5/2001 | Jackson et al. |
| 6,235,951 B1 | 5/2001 | Sakyu et al. |
| 6,472,573 B1 | 10/2002 | Yamamoto |
| 6,518,467 B2 | 2/2003 | Tung et al. |
| 6,538,167 B1 | 3/2003 | Brown |
| 6,545,176 B1 | 4/2003 | Tsay |
| 6,551,469 B1 | 4/2003 | Nair |
| 6,610,177 B2 | 8/2003 | Tsay |
| 6,613,127 B1 | 9/2003 | Galloway |
| 6,683,216 B1 | 1/2004 | Zoeller |
| 6,825,383 B1 | 11/2004 | Dewkar |
| 6,924,403 B2 | 8/2005 | Barnes et al. |
| 6,958,135 B1 | 10/2005 | Filippi |
| 7,117,934 B2 | 10/2006 | Lomax |
| 7,140,558 B2 * | 11/2006 | McCracken .......... B01F 5/0256 239/422 |
| 7,172,733 B2 * | 2/2007 | Gauthier ............. B01F 3/04049 239/398 |
| 7,189,884 B2 | 3/2007 | Mukhopadhyay |
| 7,226,567 B1 | 6/2007 | Olbert |
| 7,282,120 B2 | 10/2007 | Braun |
| 7,297,814 B2 | 11/2007 | Yada et al. |
| 7,345,209 B2 | 3/2008 | Mukhopadhyay |
| 7,371,904 B2 | 5/2008 | Ma et al. |
| 7,378,559 B2 | 5/2008 | Verwijs |
| 7,396,965 B2 | 7/2008 | Mukhopadhyay |
| 7,511,101 B2 | 3/2009 | Nguyen |
| 7,521,029 B2 | 4/2009 | Guetlhuber |
| 7,588,739 B2 | 9/2009 | Sugiyama |
| 7,659,434 B2 | 2/2010 | Mukhopadhyay |
| 7,674,939 B2 | 3/2010 | Mukhopadhyay |
| 7,687,670 B2 | 3/2010 | Nappa |
| 7,695,695 B2 | 4/2010 | Shin |
| 7,714,177 B2 | 5/2010 | Mukhopadhyay |
| 7,836,941 B2 | 11/2010 | Song |
| 7,880,040 B2 | 2/2011 | Mukhopadhyay |
| 7,951,982 B2 | 5/2011 | Mukhopadhyay |
| 8,058,486 B2 | 11/2011 | Merkel et al. |
| 8,058,490 B2 | 11/2011 | Strebelle |
| 8,071,825 B2 | 12/2011 | Johnson et al. |
| 8,071,826 B2 | 12/2011 | Van Der Puy |
| 8,076,521 B2 | 12/2011 | Elsheikh |
| 8,084,653 B2 | 12/2011 | Tung |
| 8,115,038 B2 | 2/2012 | Wilson |
| 8,123,398 B2 | 2/2012 | Teshima |
| 8,158,836 B2 | 4/2012 | Pigamo |
| 8,232,435 B2 | 7/2012 | Sievert |
| 8,258,353 B2 | 9/2012 | Tirtowidjojo |
| 8,258,355 B2 | 9/2012 | Merkel |
| 8,357,828 B2 | 1/2013 | Okamoto et al. |
| 8,367,867 B2 | 2/2013 | Zardi et al. |
| 8,383,867 B2 | 2/2013 | Mukhopadhyay |

(56) References Cited

U.S. PATENT DOCUMENTS

| | | | |
|---|---|---|---|
| 8,395,000 B2 | 3/2013 | Mukhopadhyay | |
| 8,398,882 B2 | 3/2013 | Rao | |
| 8,487,146 B2 | 7/2013 | Wilson | |
| 8,558,041 B2 | 10/2013 | Tirtowidjojo et al. | |
| 8,581,011 B2 | 11/2013 | Tirtowidjojo et al. | |
| 8,581,012 B2 | 11/2013 | Tirtowidjojo et al. | |
| 8,614,361 B2 | 12/2013 | Suzuki | |
| 8,614,363 B2 | 12/2013 | Wilson et al. | |
| 8,907,148 B2 | 12/2014 | Tirtowidjojo et al. | |
| 8,926,918 B2 | 1/2015 | Tirtowidjojo et al. | |
| 8,933,280 B2 | 1/2015 | Tirtowidjojo et al. | |
| 8,957,258 B2 | 2/2015 | Okamoto et al. | |
| 9,056,808 B2 | 6/2015 | Tirtowidjojo et al. | |
| 9,067,855 B2 | 6/2015 | Grandbois et al. | |
| 2001/0018962 A1 | 9/2001 | Joshi et al. | |
| 2002/0087039 A1 | 7/2002 | Tung et al. | |
| 2002/0110711 A1 | 8/2002 | Boneberg et al. | |
| 2006/0150445 A1 | 7/2006 | Redding | |
| 2006/0292046 A1 | 12/2006 | Fruchey | |
| 2007/0197841 A1 | 8/2007 | Mukhopadhyay | |
| 2007/0197842 A1 | 8/2007 | Tung | |
| 2007/0259296 A1* | 11/2007 | Knoepfel | F23D 17/002 431/9 |
| 2007/0265368 A1 | 11/2007 | Rao et al. | |
| 2008/0021229 A1 | 1/2008 | Maughon | |
| 2008/0073063 A1 | 3/2008 | Clavenna et al. | |
| 2008/0118018 A1 | 5/2008 | Schrauwen | |
| 2008/0207962 A1 | 8/2008 | Rao | |
| 2009/0018377 A1 | 1/2009 | Boyce | |
| 2009/0030249 A1 | 1/2009 | Merkel et al. | |
| 2009/0088547 A1 | 4/2009 | Schamshurin et al. | |
| 2009/0099396 A1 | 4/2009 | Mukhopadhyay | |
| 2009/0117014 A1 | 5/2009 | Carpenter | |
| 2009/0203945 A1 | 8/2009 | Mukhopadhyay | |
| 2009/0270568 A1 | 10/2009 | Strebelle et al. | |
| 2010/0041864 A1 | 2/2010 | Kadowaki et al. | |
| 2010/0185029 A1 | 7/2010 | Elsheikh | |
| 2010/0263278 A1 | 10/2010 | Kowoll et al. | |
| 2011/0087056 A1 | 4/2011 | Tirtowidjojo et al. | |
| 2011/0155942 A1 | 6/2011 | Pigamo et al. | |
| 2011/0172472 A1 | 7/2011 | Sakyu | |
| 2011/0218369 A1 | 9/2011 | Elsheikh et al. | |
| 2011/0251425 A1 | 10/2011 | Penzel | |
| 2012/0065434 A1 | 3/2012 | Nose | |
| 2014/0081055 A1 | 3/2014 | Tirtowidjojo | |
| 2014/0163266 A1 | 6/2014 | Tirtowidjojo et al. | |
| 2014/0179962 A1 | 6/2014 | Tirtowidjojo et al. | |
| 2014/0323775 A1 | 10/2014 | Grandbois et al. | |
| 2014/0323776 A1 | 10/2014 | Grandbois et al. | |
| 2014/0336425 A1 | 11/2014 | Tirtowidjojo et al. | |
| 2014/0336431 A1 | 11/2014 | Tirtowidjojo et al. | |
| 2014/0371494 A1 | 12/2014 | Tirtowidjojo et al. | |
| 2015/0045592 A1 | 2/2015 | Grandbois et al. | |
| 2015/0057471 A1 | 2/2015 | Tirtowidjojo et al. | |
| 2015/0217256 A1 | 8/2015 | Tirtowidjojo et al. | |

FOREIGN PATENT DOCUMENTS

| | | |
|---|---|---|
| CN | 101492341 | 7/2009 |
| CN | 101544535 | 9/2009 |
| CN | 101597209 | 12/2009 |
| CN | 101754941 | 6/2010 |
| CN | 101913979 | 12/2010 |
| CN | 101913980 | 12/2010 |
| CN | 101955414 | 1/2011 |
| CN | 101982227 | 3/2011 |
| CN | 102001911 | 4/2011 |
| CN | 102249846 | 11/2011 |
| CN | 102351637 | 2/2012 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |
| EP | 0164798 | 12/1985 |
| EP | 0453818 | 10/1991 |
| EP | 1018366 | 12/2000 |
| EP | 1097984 | 5/2001 |
| FR | 1546709 | 11/1968 |
| GB | 471186 | 8/1937 |
| GB | 471187 | 8/1937 |
| GB | 471188 | 8/1937 |
| GB | 857086 | 12/1960 |
| GB | 1134585 | 11/1968 |
| GB | 1381619 | 1/1975 |
| GB | 1548277 | 7/1979 |
| JP | 1979004869 | 1/1979 |
| JP | 54079207 | 6/1979 |
| JP | S54-135712 | 10/1979 |
| JP | 08-119885 | 5/1996 |
| JP | 2001213820 | 8/2001 |
| JP | 2006272267 | 10/2006 |
| JP | 2007021396 | 2/2007 |
| JP | 2008063314 | 3/2008 |
| JP | 2009000592 | 1/2009 |
| JP | 2009046653 | 3/2009 |
| JP | 2001151708 | 6/2011 |
| JP | 2011144148 | 7/2011 |
| LU | 52247 | 12/1966 |
| SU | 899523 | 1/1982 |
| WO | 8201728 | 5/1982 |
| WO | 9906314 | 2/1999 |
| WO | 0138271 | 5/2001 |
| WO | 0138275 | 5/2001 |
| WO | 2005016509 | 2/2005 |
| WO | 2007079431 | 7/2007 |
| WO | 2007079435 | 7/2007 |
| WO | 2007096383 | 8/2007 |
| WO | 2008054781 | 5/2008 |
| WO | 2009015304 | 1/2009 |
| WO | 2009067571 | 5/2009 |
| WO | 2009087423 | 7/2009 |
| WO | 2011060211 | 5/2011 |
| WO | 2011065574 | 6/2011 |
| WO | 2012011844 | 1/2012 |
| WO | 2012081482 | 12/2012 |
| WO | 2012166393 | 12/2012 |
| WO | 2012166394 A1 | 12/2012 |
| WO | 2013082410 | 6/2013 |
| WO | 2014046970 | 3/2014 |
| WO | 2014046977 | 3/2014 |
| WO | 2014066083 | 5/2014 |
| WO | 2014100039 | 6/2014 |
| WO | 2014100066 | 6/2014 |
| WO | 2014134233 | 9/2014 |
| WO | 2014134377 | 9/2014 |
| WO | 2014164368 | 10/2014 |

OTHER PUBLICATIONS

Bai, et al., "Isomerization of Tetrachloropropene to Promote Utilization Ratio of Triallate Raw Materials", Petrochemical Technology & Application, 2007, 25(1).

Boualy, et al., "Kharasch Addition of Tetrachloromethane to Alkenes Catalyzed by Metal Acetylacetonates", "Kharasch Addition of Tetrachloromethane to Alkenes Catalyzed by Metal Acetylacetonates".

Chai, et al., "Study of Preparation of 1,1,1,3-tetrachloropropane", Zhejiang Chemical Industry, 2010, pp. 1-3, 41(5).

Cristiano, et al., "Tetraalkylphosphonium Trihalides. Room Temperature Ionic Liquids As Halogenation Reagents", J. Org. Chem., 2009, pp. 9027-9033, 74.

Evstigneev, et al., "Initiated Chlorination of Tetrachloropropane", Khim. Prom., 1984, pp. 393-394, 16(7).

Fields, et al., "Thermal Isomerization of 1,1-dichlorocyclopropanes", Chemical Communications, Jan. 1, 1967, p. 1081, 21.

Galitzenstein, et al., "The Dehydrochlorination of Propylene Dichloride", Journal of the Society of Chemical Industry, 1950, pp. 298-304, 69.

(56) References Cited

OTHER PUBLICATIONS

Gault, et al., "Chlorination of Chloroform", Comptes Rendus Des Seances De L'Academie des Sciences, 1924, pp. 467-469, 179.

Gerding, et al., "Raman Spectra of aliphatic chlorine compounds: chloroethenes an chloropropenes", Recueil Jan. 1, 1955, pp. 957-975, 74.

Hatch, et al., "Allylic Chlorides. XV. Preparation and Properties of the 1,2,3Trichloropropenes", JACS, Jan. 5, 1952, pp. 123-126, 74.

Hatch, et al., "Allylic Chlorides. XVIII. Preparation and Properties of 1,1,3-tricholoro-2-fluoro-1-propene and 1,1,2,3-tetrachloro-1-propene", JACS, Jul. 5, 1952, pp. 3328-3330, 74(13).

Herzfelder, "Substitution in the Aliphatic Series", Berichte Der Deutschen Chemischen Gesellschaft, May-Aug. 1893, pp. 1257-1261, 26(2).

Huaping, et al., "Procress in Synthesis of 1,1,1,3-tetrachloropropane", Guangzhou Chemicals, 2011, , pp. 41-42, 39(5).

Ivanov, et al., "Metal phthalocyanine-Catalyzed Addition of polychlorine-Containing Organic Compounds to C=C Bonds", Russian Chemical Bulletin, International Edition, Nov. 2009, pp. 2393-2396, 58(11).

Kang, et al., "Kinetics of Synthesis of 1,1,1,3,3-pentachlorobutane Catalyzed by Fe—FeCl3", Chemical Research and Application, Jun. 2011, pp. 657-660, 23(6).

Kharasch, et al., "Chlorinations with Sulfuryl Chloride.I. The Peroxide-Catalyzed Chlorination of Hydrocarbons", JACS, 1939, pp. 2142-2150, 61.

Khusnutdinov, et al., "CCI4 Attachment to Olefins Catalyzed by Chromium and Ruthenium Complexes. Impact of Water as a Nucleophilic Admixture", Oil Chemistry, 2009, pp. 349-356, vol. 4.

Kruper, et al., "Synthesis of alpha-Halocinnamate Esters via Solvolytic Rearrangement of Trichloroallyl Alcohols", J Org Chem, 1991, pp. 3323-3329, 56.

Leitch, "Organic Deuterium Compounds: V. The chlorination of propyne and propyne D-4", Canadian Journal of Chemistry, Apr. 1, 1953, pp. 385-386, 30(4).

Levanova, et al., "Cholorination of Chloroolefins C3—C4", 2002, 496-498.

Levanova, et al., "Thermocatalytic Reactions of Bromochloropropanes", Russian Journal of Physical Chemistry, Jan. 1, 1983, pp. 1142-1146, 57.

McBee, et al., "Utilization of Polychloropropanes and Hexachloroethane", Industrial and Engineering Chemistry, Feb. 1, 1941, pp. 176-181, 33(2).

Mouneyrat, "Effect of Chlorine on Propyl Chloride in the Presence of Anhydrous Aluminum Chloride", Bulletin de la Societe chimique de france, Societe francaise de chimie, Jan. 1, 1899, pp. 616-623, 21(3).

Munoz-Molina, et al., "An Efficient, Selective and Reducing Agent-Free Copper Catalyst for the Atom-Transfer Radical Addition of Halo Compounds to Activated Olefins", Inorg. Chem., 2010, pp. 643-645, 49.

Nair, et al., "Atom Transfer Radical Addition (ATRA) of Carbon Tetrachloride and Chlorinated Esters to Various Olefins Catalyzed by CP/Ru(PPh3)(PR3)CI Complexes", Inorganica Chimica Acta, 2012, pp. 96-103, 380.

Nguyen, et al., "Condensation de chloroforme avec des olefins fluorees en milieu basique", Journal of Fluorine Chemistry, Dec. 1, 1991, pp. 241-248, 55(3).

Nikishin, et al., "Reactions of Methanol and Ethanol with Tetrachloroethylene", Izvestiya Akademii Nauk SSSR, Seriya Khimicheskaya, Dec. 1966, pp. 2188-2192, 12.

Ochi, et al., "Preparation of Chloropropenes by Photochemical Dehydrochlorination of 1,2-Dichloropropane", Chemical Abstracts, Jul. 17, 1989, p. 574, 111(3).

Pozdnev, et al., "Chlorination of chloroform and the conversion of methylene chloride manufacture still residues", Khim., Khim. Tekhnol., 1970, 70(4).

Rotshtein, et al., "Isomer Distribution on Chlorination of Chloropropanes", Z. Organicheskoi Khimii, 1966, pp. 1539-1542, 2(9).

Semenov, "Selectivity of Photochemical Chlorination of Chloromethane in the Liquid Phase", Prikladnei Khimii, 1985, pp. 840-845, 58(4).

Shelton, et al., "Addition of Halogens and Halogen Compounds to Allylic Chlorides. I. Addition of Hydrogen Halides", Journal of Organic Chemistry, 1958, pp. 1876-1880, 23.

Skell, et al., "Reactions of BrCl with alkyl radicals", Tetrahedron letters, 1986 pp. 5181-5184, 27(43).

Skell, et al., "Selectivities of pi and sigma succinimidyl radicals in substitution and addition reactions, Response to Walling, Wl-Taliawi and Zhao", JACS, Jul. 1, 1983, pp. 5125-5131, 105(15).

Stevens, "Some New Cyclopropanes with a Note on the Exterior Valence Angles of Cyclopropane", JACS, Vo. 68, No. 4, 1945, 620-622.

Tanuma, et al., "Partially Fluorinated Metal Oxide Catalysts for a Friedel-Crafts-type Reaction of Dichlorofluoromethane with Tetrafluoroethylene", Catal. Lett., 2010, pp. 77-82, 136.

Tobey, et al., "Pentachlorocyclopropane", Journal of the American Chemical Society, Jun. 1, 1996, pp. 2478-2481, 88 (11).

Urry, et al., "Free Radical Reactions of Diazomethane with Reactive Bromopolychloroalkane", JACS, May 5, 1964, pp. 1815-1819, 86(9.

Wang Chin-Hsien, "Elimination Reactions of polyhalopropanes under emulsion catalytic conditions to give Halopropenes", Synthesis, Jan. 1, 1982, pp. 494-496, 1982(6).

Zhao, et al., "Research Progress on Preparation Technology of 1,1,2,3-Tetrachloropropene", Zhejiang Chemical Industry, 2010, pp. 8-10, 41(6).

Zheng, et al., "Preparation of the low GWP alternative 1,3,3,3-tetrafluoropropene", Zhejiang Huagong, 2010, pp. 5-7, 41(3).

Japanese Publication No. 2015-536816 Office Action dated Jan. 9, 2018.

* cited by examiner

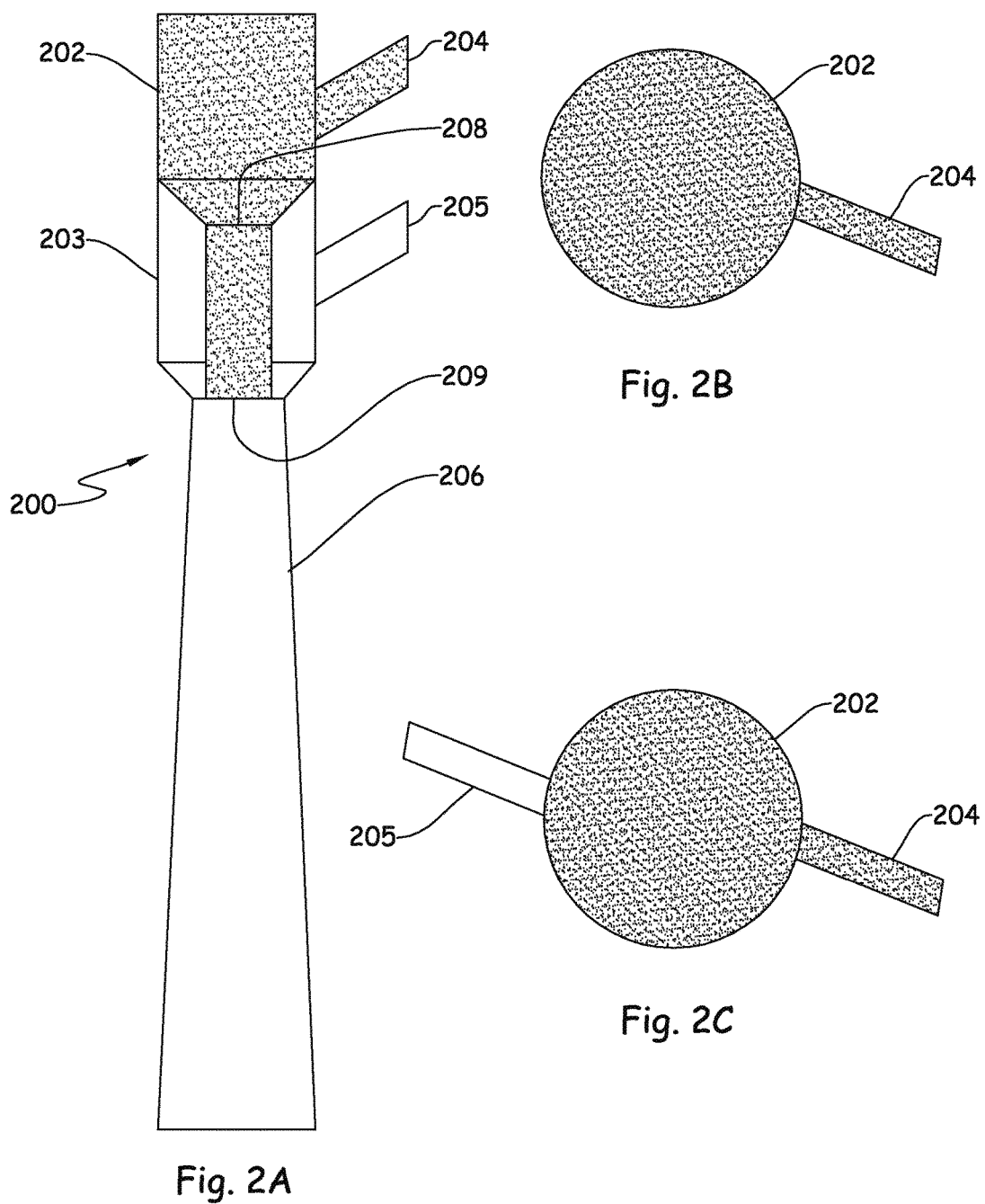

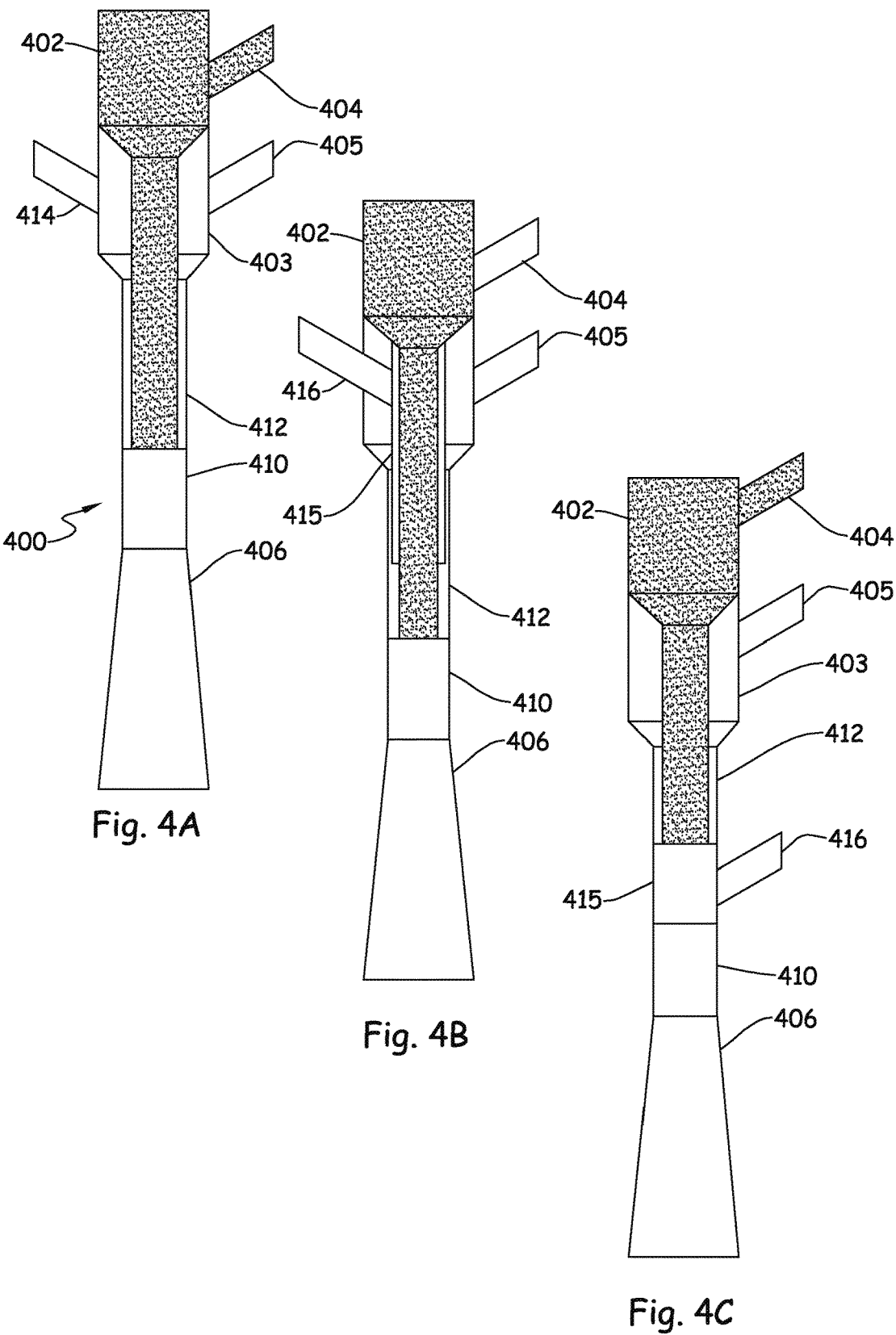

MIXER AND PROCESSES INCORPORATING THE SAME

FIELD

The present invention relates to an efficient and effective mixer, an apparatus comprising the mixer and a reactor, and processes incorporating the same.

BACKGROUND

Hydrofluorocarbon (HFC) products are widely utilized in many applications, including refrigeration, air conditioning, foam expansion, and as propellants for aerosol products including medical aerosol devices. Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoroolefin (HFO) products. Relative to their predecessors, HFOs are expected to exert less impact on the atmosphere in the form of a lesser or no detrimental impact on the ozone layer and their much lower GWP as compared to HFC's. Advantageously, HFO's also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene or 1,3,3, 3-tetrafluoroprop-1-ene, may typically be produced utilizing feedstocks of chlorocarbons or chlorofluorocarbons, and in particular, chlorinated propenes.

Unfortunately, many chlorinated propenes may have limited commercial availability, and/or may only be available at potentially prohibitively high cost, due at least in part to the propensity of the conventional processes typically utilized in their manufacture to result in the production of large quantities of secondary products, i.e., waste and/or by-products. Any such secondary products produced not only have to be separated from the final product and disposed of, but also, can result in system fouling prior to doing so. Both of these outcomes can introduce substantial expense, further limiting the commercial potential of processes in which the production of such secondary products is not reduced or eliminated. Further, these problems become exacerbated on process scale-up, so that large scale processes can become cost prohibitive quickly.

In many conventional processes for the production of chlorinated propenes, formation of excessive secondary products can be difficult to avoid since many such processes require only partial conversion of the limiting reagents. Greater conversions can result in the production of large quantities of secondary products. Excessive conversion, in turn, can be caused by backmixing of reactants and/or products.

Various mixers have been developed in efforts to minimize backmixing of reactants that may occur prior to entry into the reactor; however, none of these are without detriment. For example, mixers have been provided having the same diameter as the reactor so that backmixing zones are not created at the junction there between. When coupled with appropriate introduction of reactants, these mixers have proven effective, but can yet be suboptimal.

First, building a mixer with the same large diameter, e.g., up to 8 feet, as many reactors for the production of chlorinated propenes can be costly. Furthermore, the use of large diameter mixers can make the desired flow distribution within the mixer difficult to obtain due to the drop in pressure and velocity of the reactants upon entry into the mixer from their respective feed lines.

It would thus be desirable to provide improved mixers for use in methods wherein limiting reactants are desirably utilized. More particularly, mixers that provide quick and thorough mixing of two or more reactants, while yet also minimizing back mixing of the mixed feed stream and thus providing a reduction in the amount of secondary products that are produced would be welcomed in the art. Further advantage would be seen if such mixers could be provided cost effectively, i.e., on a smaller scale than the reactors with which they are desirably utilized.

BRIEF DESCRIPTION

A mixer that provides such advantages is provided herein. More specifically, the mixer incorporates an expander zone, wherein the inner diameter thereof expands outwardly at an angle of less than 90° relative to a longitudinal axis of the expander zone. In this way, a mixer can be provided having an inlet diameter smaller than its exit diameter, so that when coupled to a reactor, any backmixing zone that may otherwise be provided by disparate geometries between the mixer outlet and reactor inlet can be minimized or eliminated. The mixer may also incorporate one or more chambers, flow pattern development zones, and/or mixing zones that can act alone or together to improve the flow and/or mixing of the reactants therein so that uniform and efficient mixing is provided by the mixer. As a result, desired conversions may be substantially maintained, formation of secondary products may be minimized and/or fouling may be reduced or eliminated. And so, in addition to the cost savings that may be provided by manufacturing a mixer having a smaller inlet diameter than a reactor inlet diameter, savings are further provided by minimizing, or avoiding entirely, the costs associated with separating and disposing of, secondary products and/or process downtime to clean foulants from the system.

In one aspect of the present invention, a mixer is provided. The mixer comprises at least one inlet to at least one chamber, and an expander zone. The angle created by a longitudinal axis of the chamber and a longitudinal axis of the inlet (hereinafter the 'chamber-inlet angle', or α in FIG. 1A) is less than 90°, or may be from 30° to 80°. The inner diameter of the expander zone ($D_e$) expands outwardly at an angle (hereinafter the 'expander angle' or β in FIG. 1A) less than 90°, or less than 45°, or less than 20°, or less than 15°, or even less than 10° relative to a longitudinal axis of the expander zone. The chamber has an inner diameter ($D_c$) that is at least 1.25, or at least 2 times greater than the inner diameter of its inlet ($D_{ci}$). In some embodiments, the inner diameter of the chamber ($D_c$) may be from 2-10 times greater than the inner diameter of its inlet ($D_{ci}$).

The chamber also desirably comprises an outlet, and in those embodiments wherein multiple chambers/inlets are utilized, the outlets thereof are desirably arranged concentrically, i.e., so that two concentrically placed outlets create an annular space there between. The ratio of the cross sectional area of each annular space ($A_a$) to the area of the inner most chamber outlet ($A_{co}$, innermost) is desirably between 1 and 3, i.e., $A_a/A_{co}$ is between 1 and 3. The chamber inner diameter ($D_c$) may taper to the inner diameter of the chamber outlet ($D_{co}$), or, the chamber inner diameter ($D_c$) may decrease at a 90° angle to provide the chamber outlet.

The chamber outlet has an inner diameter ($D_{co}$) that is at least 2 times greater than the inner diameter of the chamber inlet ($D_{ci}$). The outlet has an inner diameter ($D_{co}$) that is less than the chamber inner diameter ($D_c$), e.g., the ratio of the chamber inner diameter ($D_c$) to the outlet inner diameter ($D_{co}$) may be at least 1, or at least 1.1, or at least 1.2. Desirably, the ratio of the inner diameter of the chamber ($D_c$) to the inner diameter of its outlet ($D_{co}$) is less than 10, or less than 8, or less than 6, or less than 5, or less than 4. In some embodiments, the ratio of the inner diameter of the chamber ($D_c$) to the inner diameter of its outlet ($D_{co}$) is from 1.1 to 8 or from 1.2-4. In some embodiments, the inner diameter of the chamber ($D_c$) and the inner diameter of its outlet ($D_{co}$) may be approximately the same.

In some embodiments, the mixer may additionally comprise a flow pattern development zone and/or a mixing zone. If utilized, the flow pattern development zone may be an extension of the chamber outlet(s), i.e., may be a series of concentrically placed tubes creating an inner tube and a series of annular spaces. The length of any flow pattern development zone ($L_{fpd}$) may desirably be substantially the same as, or greater than, the diameter of the outermost tube ($D_{fpd}$) within the flow development zone. If both a mixing zone and a flow pattern development zone are utilized, the mixing zone is desirably downstream of the flow pattern development zone. In any case, the mixing zone may desirably comprise a single tube having an inner diameter ($D_m$) less than or equal to that of the outermost chamber outlet ($D_{co}$, outermost), or the outermost tube of the flow pattern development zone ($D_{fpd}$), as the case may be. The combined mixing zone and flow pattern development zone, if any, has a length ($L_{fpd}+L_m$) 3 times greater, or 9 times greater, than the inner diameter ($D_m$) of the mixing zone.

The advantageous features and dimensional relationships of the mixer may be taken advantage of when the mixer is utilized in connection with a reactor, and indeed, additional dimensional relationships between the mixer and reactor inlet have been discovered that further assist in realizing, or further leveraging, the full benefits of both. And so, in another aspect, there is provided an apparatus comprising a reactor having an inlet with an inner diameter ($D_r$) and a mixer comprising at least one inlet to at least one chamber, wherein the chamber outlet inner diameter ($D_{co}$), flow pattern development zone inner diameter ($D_{fpd}$) and/or mixing zone inner diameter ($D_m$) is/are less than that of the reactor inlet inner diameter ($D_r$). The ratio of the inner diameter of the reactor ($D_r$) to the chamber outlet inner diameter ($D_{cp}$), flow pattern development zone inner diameter ($D_{fpd}$) and/or mixing zone inner diameter ($D_m$) is desirably from 2 to 5, or from 3 to 4. The mixer also comprises an expander zone having an inner diameter ($D_e$) that expands outwardly at an angle of less than 90°, or less than 45°, or less than 20°, or less than 10°. The reactor may have an inner diameter of more or less than 4 feet. The reactor and/or mixer may comprise one or more bends of 90 degrees or greater, to accommodate the desired design and length thereof easily in the available manufacturing space.

Since the present apparatus are expected to provide time and cost savings to the gaseous processes in which they are utilized, such processes are also provided. Processes comprising a limiting reagent find particular benefit.

In another aspect, processes for mixing at least two reagents for a chemical process are provided. The processes comprise providing the at least two reactants to an apparatus comprising a reactor having an inner diameter ($D_r$) and a mixer comprising at least one inlet to at least one chamber, wherein the chamber outlet inner diameter ($D_{co}$), flow pattern development zone inner diameter ($D_{fpd}$) and/or mixing zone inner diameter ($D_m$) is/are less than that of the reactor inlet inner diameter ($D_r$). The ratio the inner diameter of the reactor ($D_r$) to the outermost chamber outlet inner diameter $D_{co}$ and/or the mixing zone inner diameter ($D_m$) is desirably from 2 to 6, or from 3 to 5. The mixer also comprises an expander zone having an inner diameter ($D_e$) that expands outwardly at an angle of less than 90°, or less than 45°, or less than 20°, or less than 10°.

BRIEF DESCRIPTION OF THE DRAWINGS

These and other features, aspects, and advantages of the present invention will become better understood when the following detailed description is read with reference to the accompanying drawings, wherein:

FIG. 2A is a schematic representation (not to scale) of one embodiment of the mixer comprising two inlets/chambers and an expander zone;

FIG. 2B is a top view of one arrangement of the chamber inlets of the embodiment shown in FIG. 2A;

FIG. 2C is a top view of a further arrangement of the chamber inlets of the embodiment shown in FIG. 2A;

FIG. 4A is a schematic representation (not to scale) of one embodiment of the mixer comprising three inlets and two chambers, a flow pattern development zone, a mixing zone and an expander zone, wherein two inlets are provided on one chamber;

FIG. 4B is a schematic representation (not to scale) of one embodiment of the mixer comprising three inlets/chambers, a flow pattern development zone, a mixing zone and an expander zone, wherein a third chamber is provided within the second chamber; and FIG. 4C is a schematic representation (not to scale) of one embodiment of the mixer comprising three inlets/chambers, a flow pattern development zone, a mixing zone and an expander zone, wherein a third chamber and corresponding inlet is provided between the flow pattern development zone and the mixing zone.

DETAILED DESCRIPTION

Figures 1A, 1B, 1C:
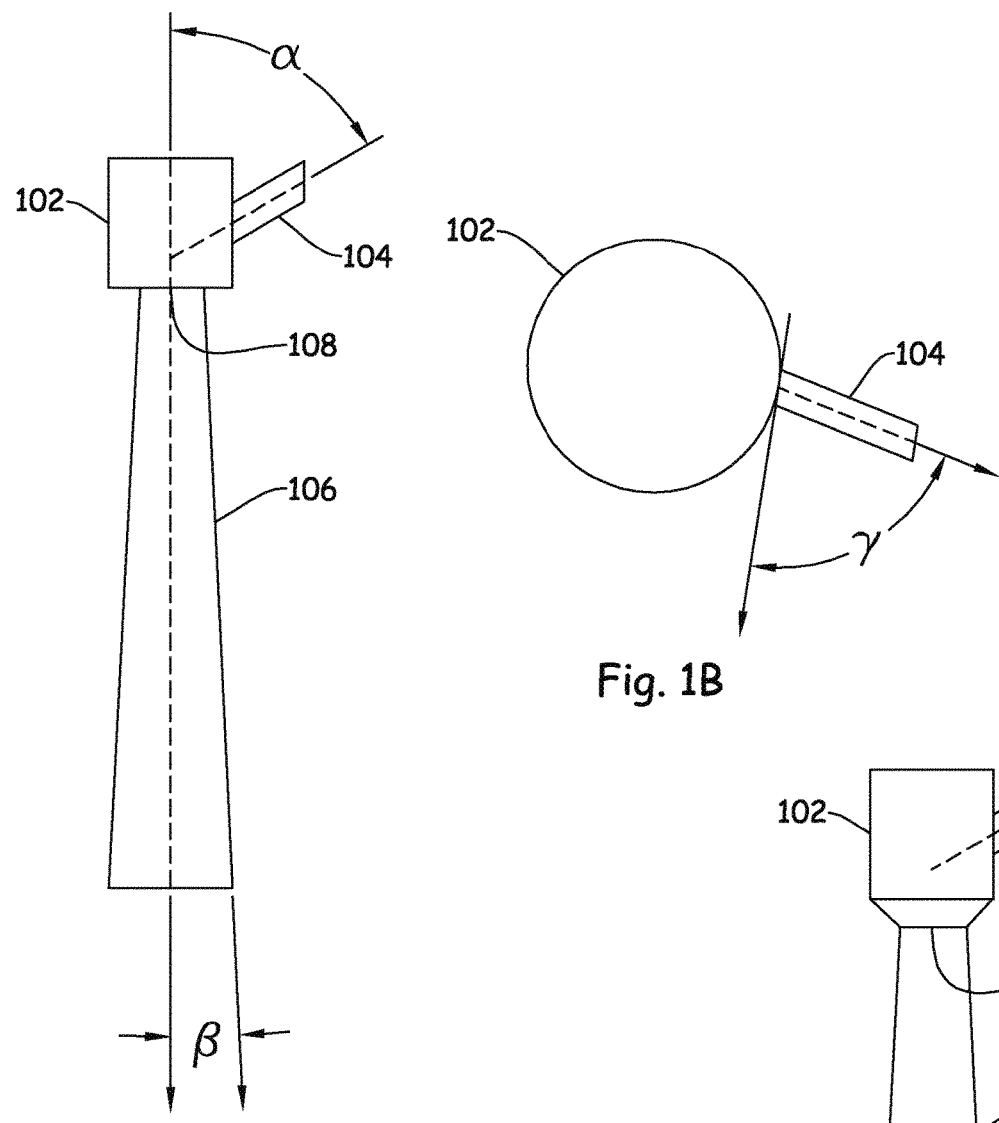
FIG. 1A is a schematic representation (not to scale) of one embodiment of the mixer comprising one inlet/chamber and an expander zone.
FIG. 1B is a top view of the schematic representation of the embodiment shown in FIG. 1A.
FIG. 1C is a schematic representation (not to scale) of the mixer shown in FIG. 1, further comprising a taper from the chamber inner diameter to provide the chamber outlet.

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not intended to limit the part being described limited to any one position or spatial orientation.

If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

The mixer provided herein may incorporate one or more angles between components, zones, or longitudinal axes thereof that provide the mixer with improved performance relative to mixers not incorporating the angle. In each instance, the angles are defined as the lesser angle of the linear pair created by, or that would be created by, the intersection of the components, zones, or axes. For example, the chamber-inlet angle (denoted "α" in FIG. 1A) is defined as the lesser angle of the linear pair created by the intersection of the longitudinal axes of the chamber and the longitudinal axes of its inlet. Similarly, the expander angle (denoted "β" in FIG. 1A) is defined as the lesser angle of the linear pair created by the intersection of the longitudinal axis of the expander zone and a line extended from the inner diameter of the expander zone to intersect with the longitudinal axis of the expander zone. Finally, the transverse chamber-inlet angle (denoted "γ" in FIG. 1B) is defined as the lesser angle of the linear pair created by the intersection of the longitudinal axis of the inlet and a line tangential to the chamber projected on a cross sectional plane to the chamber intersecting the point where the longitudinal axis of the inlet line meets the chamber's wall.

The present invention provides a mixer for use in a gas-phase process, such as processes for the production of chlorinated propenes and/or higher alkenes. The mixer incorporates one or more design features that can i) provide for reduced backmixing of the reactants, and/or ii) minimize or eliminate plugging within the mixer. As a result, desired conversions may be substantially maintained, formation of secondary products may be minimized and/or fouling may be reduced or eliminated. Further, the advantages provided by one design feature may be leveraged, perhaps even synergistically, by combining the same with others.

More specifically, the mixer comprises an inlet fluidly connected to a chamber, wherein the chamber-inlet angle ($\alpha$) is less than 90°. Desirably, the chamber-inlet angle, $\alpha$, is less than 15°, or less than 80°. In some embodiments, the chamber-inlet angle ($\alpha$) may be greater than 20°, or greater than 30°. In some embodiments, the chamber-inlet angle ($\alpha$) may be from 30°-80°. The mixer also comprises an expander zone, wherein the inner diameter thereof expands outwardly along the length thereof at an expander angle ($\beta$) of less than 90°, or less than 45°, or less than 20°, or less than 15°, or less than 10°. Desirably, expander angle $\beta$ is greater than 1°, or greater than 2°, or greater than 3°, or greater than 4°, or greater than 5°. In some embodiments, expander angle $\beta$ may be from 1° to 90°, or from 2° to 45°, or from 3° to 20°, or from 4° to 15°, or from 5° to 10°. At its outlet, the expander may have an inner diameter ($D_e$) of less than 100 feet, or less than 80 feet, or less than 50 feet, or less than 20 feet. In some embodiments, the expander zone outlet inner diameter ($D_e$) may be substantially equal to the reactor inlet inner diameter ($D_r$)

The combination of these two features has been discovered to provide a mixer that not only provides the desired flow pattern and efficient mixing, but also is inexpensive to manufacture and robust in the challenging environments created by processes for the production of chlorinated propenes. More particularly, the provision of a chamber inlet angle $\alpha$ less than 90°, or from 30°-80° has been found to render the mixer more robust against fouling from contaminants and secondary products that may already be present in the reactants as they are presented to the mixer. And, the provision of an expander zone, incorporating an expander angle $\beta$ of less than 90°, allows the mixer to include an inlet close in size to the typical size of feedstreams used in commercial chemical processes, but yet, an outlet that may more closely approximate the size of the inlet of a reactor to which the mixer may be coupled. As such, the pressure drop and/or backmixing that may otherwise be seen between mixers and feedstreams, or mixers and reactors, of disparate sizes can be minimized or avoided.

In some embodiments, the chamber may exhibit substantially the same geometry as the inlet, and the geometries thereof may be selected to encourage a desired flow pattern. Any flow pattern can be established and encouraged by the mixer (with the exception of back mixed flow). In some embodiments, the mixer is desirably utilized to produce a swirling flow pattern. Swirling flow patterns can be advantageous for use in many chemical processes, but in particular in processes where backmixing can be an issue. This is because swirling flow patterns tend to produce high shear at internal surfaces that can assist in the prevention of the accumulation of solids thereon. Swirling flow patterns may also only require a small head mixing chamber in comparison to the reactor diameter in order to be established. A swirling flow pattern can be induced by introduction of a feedstream into a generally cylindrical inlet, and thereafter into a generally cylindrical chamber.

The inlet and chamber may have the same, or a different, inner diameter. In some embodiments, advantage can be seen by providing the chamber with an inner diameter ($D_c$) at least 1.25 times greater, or at least two times greater, than the inner diameter of the inlet ($D_{ci}$). In some embodiments, the inner diameter of the chamber ($D_c$) is desirably less than 20 times, or less than 10 times, the inner diameter of the chamber inlet ($D_{ci}$). In some embodiments, the ratio of the inner diameter of the chamber ($D_c$) to the inner diameter of the inlet ($D_{ci}$) is from 2-10. Providing the chamber and inlet with such a dimensional relationship has been found to render the chamber and inlet robust to the presence of the particulates and/or secondary products that may be present in the feedstreams as introduced therein.

The chamber also desirably comprises an outlet, which may desirably be of the same geometry as the chamber and/or inlet. The outlet may also have the same diameter, or cross sectional area, as the case may be, as the chamber and/or chamber inlet, or may have a different diameter. In some embodiments, the chamber outlet has an inner diameter ($D_{co}$) that is at least 2 times greater than the inner diameter of the chamber inlet ($D_{ci}$). The outlet has an inner diameter ($D_{co}$) that is less than the chamber inner diameter ($D_c$), e.g., the ratio of the chamber inner diameter ($D_c$) to the outlet inner diameter ($D_{co}$) may be at least 1, or at least 1.1, or at least 1.2. Desirably, the ratio of the inner diameter of the chamber ($D_c$) to the inner diameter of its outlet ($D_{co}$) is less than 10, or less than 8, or less than 6, or less than 5, or less than 4. In some embodiments, the ratio of the inner diameter of the chamber ($D_c$) to the inner diameter of its outlet ($D_{co}$) is from 1.1 to 8 or from 1.2-4.

If two or more inlets/chambers are provided, the outlets of any provided proximate to each other are desirably provided as concentric rings. In this way, the innermost chamber outlet would act as an egress for one reactant. Each subsequent chamber outlet would provide an annular space between it and the chamber outlet immediately interior to it, through which an additional reactant may flow, and so forth. The ratio of the cross sectional area of each annular space ($A_a$) to the area of the inner most chamber outlet ($A_{co}$, innermost) is desirably between 1 and 3, i.e., $A_a/A_{co}$ is between 1 and 3.

In some embodiments more than one, more than two, or more than three, or even more than 4, inlet(s)/chamber(s) are provided. In some embodiments, at least two inlets/chambers are provided. In other embodiments, more than one inlet may be provided on one or more chambers. In such embodiments, the additional inlet(s) and/or chamber(s) can have the same configuration, i.e., shape, inner dimension, chamber inlet angle, tangential chamber inlet angle, or one or more different configuration(s). For purposes of manufacturing efficacy, in those embodiments wherein multiple inlets/chambers are used, they may have the same configuration, but this is not necessary to appreciate the advantages of the invention.

In some embodiments, the mixer may be provided with additional features and/or dimensional relationships that further enhance its suitability for use in connection with processes comprising a limiting reagent. More particularly, in some embodiments, the mixer may further comprise an advantageous tangential chamber-inlet angle and/or a flow pattern development zone and/or a mixing zone.

That is, it has now been discovered that an angle γ between the chamber inlet and a line tangential to the chamber projected on a cross sectional plane to the chamber intersecting the point where the longitudinal axis of the inlet line meets the chamber's wall of less than 90°, or less than 80°, or less than 70°, or less than 60°, provides a beneficial flow to the reactant provided through the inlet. Desirably, the tangential chamber inlet angle γ is greater than 5°, or greater than 10°, or greater than 15°, or greater than 20°. In some embodiments, the tangential chamber inlet angle γ is from 5° to 90°, or 10° to 80°, or 15° to 70°, or 20° to 60°.

The flow pattern development zone, if provided, will desirably be of a shape and/or dimension that further encourages the formation and/or maintenance of the desired flow pattern of the reactant provided by the at least one inlet. In those embodiments wherein a swirling pattern is developed, the flow pattern development zone may comprise a tube within a tube design, wherein the number of tubes correspond to the number of reactants introduced via inlets/chambers upstream of the flow pattern development zone.

If, for example, only one reactant is provided via an inlet/chamber upstream of the flow pattern development zone, the flow development zone may simply be a tube having an inner diameter ($D_{fpd}$) approximately the same as the inner diameter of the chamber outlet ($D_{co}$) and be fluidly connected thereto. As another example, if three reactants are to be used in the process, and all three are desirably introduced upstream of the flow pattern development zone, three tubes of differing inner diameters would be provided about the same longitudinal axis. The innermost tube could be fluidly connected to a first chamber outlet, the annular space provided between the innermost tube and the next outlying tube could be fluidly connected to a second chamber outlet, and the annular space created by the middle tube and the outermost tube could be fluidly connected to a third chamber outlet.

In another embodiment wherein three reactants are used, two may be introduced via two inlet/chambers, and a third may be introduced according to any method known to those of ordinary skill in the art, and may be introduced, e.g., after a flow pattern development zone. This embodiment may be advantageous when a desired reactant has a lesser residence time within the mixer for any reason, e.g., the reactant is highly reactive, unstable at the temperature(s) at which the other reactants are introduced to the mixer, etc.

In embodiments wherein a flow pattern development zone is desirably included, it can have any suitable length ($L_{fpd}$) and inner diameter ($D_{fpd}$). Desirably, the length and inner diameter of the flow pattern development zone will facilitate and/or accommodate the desired flow rate of the reactants, while also encouraging or enhancing the desired flow pattern. The inner diameter ($D_{fpd}$) of the innermost tube of the flow pattern development zone may be greater than 0.25 inch, or greater than 0.5 inch, or greater than 0.75 inches, or greater than 1 inch. The inner diameter ($D_{fpd}$) of the outermost tube of the flow pattern development zone may be less than 60" or less than 30" or less than 24" or less than 18". In some embodiments, the inner diameter ($D_{fpd}$) of the innermost tube of the flow pattern development zone is from 0.25 to 60" of from 0.5-30", or from 0.75 to 24 inches, or from 1" to 18".

Any flow pattern development zone can have a length ($L_{fpd}$) such that the ratio of its length ($L_{fpd}$) to the inner diameter ($D_{fpd}$) of the innermost tube thereof is greater than 0.5, or greater than 0.75, or greater than 1.0, or greater than 1.25, or greater than 1.5. The ratio $L_{fpd}$ to $D_{fpd,\ innermost}$ may be less than 50, or less than 40, or less than 30, or less than 20, and in some embodiments, may be less than 10. In some embodiments, $L_{fpd}/D_{fpd,\ innermost}$ may be from 0.25-50, or from 0.5 to 40, or from 0.75 to 30, or from 1.0 to 20, or from 1.25 to 10.

A mixing zone may also be provided in some embodiments, and can be used to mix one or more reactants prior to entry into the expander zone. The mixing zone may be fluidly connected to the chamber outlet, or the flow pattern development zone, at the upstream end thereof, and is desirably fluidly connected to the expander zone at its downstream end. The mixing zone may be used to bring the reactants, previously introduced into separate inlets, and in some embodiments, passed through the flow pattern development zone, into contact with each other. The mixing zone is desirably of a geometry that will allow the flow pattern to be substantially maintained, and in some embodiments, may be cylindrical.

The mixing zone may advantageously have the same, or a lesser, inner diameter ($D_m$) as the largest immediately preceding inner diameter, i.e., if fluidly connected to one or more chamber outlets, the mixing zone is desirably substantially the same or smaller, diameter as the outermost chamber outlet. If the mixing zone is fluidly connected to a flow pattern development zone, the mixing zone will desirably be of the same geometry, and have an inner diameter, or cross sectional area, as the case may be, substantially the same as the outermost tube of the flow pattern development zone.

Any mixing zone may be of any suitable length ($L_m$), which may be chosen based upon the flow rate and reactivity of the reactants. Any mixing zone may have a length, $L_m$, of greater than 1 foot, or greater than 10 feet, or greater than 20 feet, or greater than 30 feet. Mixing zone length Lm may be less than 60 feet, or less than 50 feet, or less than 40 feet. In some embodiments, mixing zone length may be from 1 to 60 feet, or from 10 feet to 50 feet, or from 20 feet to 40 feet. The ratio of mixing zone length $L_m$ to $D_m$ may, e.g., be 1, or 2, or 6, or 10. Desirably, the ratio of mixing zone length $L_m$ to mixing zone diameter $D_m$ will be from 2 to 8.

One or more of the described features and/or dimensions may advantageously be employed in the mixer, wherein their advantages are expected to be cumulative, and perhaps synergistic. Any two, any three, any four, any five or all of the design concepts may be employed. For example, the mixer may have an chamber-inlet angle α of less than 90°, an expander zone having an expander angle β of ≤45°, and/or i) a chamber inner diameter ($D_c$) at least 1.25 times greater than the inner diameter of the chamber inlet ($D_{ci}$), and/or ii) a chamber inner diameter ($D_c$) that is at least the same or greater than the inner diameter of the chamber outlet ($D_{co}$), and/or iii) a tangential chamber-inlet angle α of less than 90°, and/or iv) a flow pattern development zone, having a ratio of length ($L_{fpd}$) to the inner diameter ($D_{fpd}$) of at least 0.5 and/or a mixing zone having a ratio of length ($L_m$) and inner diameter ($D_m$) of at least 1.0.

Tables 1 and 2 show the possible dimensional relationships that may be optimized in the present mixer and possible values/ranges for each. More particularly, Table 1 contemplates the addition of any number of reactants to the mixer, and Table 2 is directed to those embodiments wherein 2 reactants are introduced via inlets/chambers (although others may be introduced by other means, into other sections of the mixer, e.g., as via injection into a port, etc.)

TABLE 1

| Dimension | Embodiment 1 | Embodiment 2 | Embodiment 3 |
| --- | --- | --- | --- |
| Number of inlets/chambers | 2 or greater | 2-10 | 2-5 |
| $D_c$ (inches) | 0.5-120 | 0.75-90 | 1.25-60 |
| $D_c/(D_{ci})$ | 1.25-20 | 1.5-20 | 2-10 |
| Chamber-inlet angle, α | ≠90° | 5°-85° | 10°-80° |
| Tangential chamber-inlet angle, γ | 0° or greater | 60° to 85° | 70° to 80° |
| $D_c/D_{co}$ | 1-10 | 1.2-8 | 1.2-4 |
| $D_{fpd,\ innermost}$ | 0.5-60 | 0.5-30 | 1-24 |
| $L_{fpd}/D_{fpd,\ innermost}$ | 0.5-30 | 1-20 | 1-10 |
| $D_{fpd,\ outermost}$ | NA-60 | NA-50 | NA-40 |
| $L_m$ (feet) | 0-60 | 0-50 | 0-40 |
| $D_m$ (inches) | 0.5-120 | 1.0-60 | 1.0-36 |
| Expander angle (β) | ≤90° | 2-45° | 3-25° |
| $D_e$ (feet) | ≤100 | ≤50 | ≤20 |

One exemplary embodiment of the mixer is shown in FIG. 1. As shown, mixer 100 includes chamber 102, inlet 104, and expander 106, wherein chamber inlet angle, a, is from 10-80°, or 60° and expander angle β that is desirably >0° but is <25°. FIG. 1B shows a top view of the mixer shown in FIG. 1A, showing the tangential chamber-inlet angle γ, which is desirably from 10° to 80°. In the embodiment shown in FIG. 1A, chamber outlet 108 is provided by a decrease of 90° in the chamber inner diameter. FIG. 1C shows an embodiment wherein the chamber inner diameter is tapered to provide chamber outlet 108. Mixer 100 may accommodate the introduction of one or more reagents/reactants via inlet 104. Additional reactants/reagents may be introduced at other conventional inlets provided in mixer 100, such as injection ports (not shown).

Another embodiment of the mixer is shown in FIG. 2. Mixer 200 includes two chambers 202 and 203 and inlets 204 and 205, wherein both chambers are tapered to provide chamber outlets 208 and 209, respectively. FIG. 2B shows a top view of mixer 200, wherein inlets 204 and 205 are arranged so as to appear superimposed when viewed from the top of mixer 200. FIG. 2C shows an alternative arrangement of inlets 204 and 205 to that shown in FIGS. 2A and 2B. Mixer 200 can accommodate the introduction of one or more reactants via inlet 204, one or more reactants via inlet 205, and any number of additional reactants introduced by, e.g., injection ports (not shown) as may be provided in mixer 200.

Figures 3A, 3B, 3C:
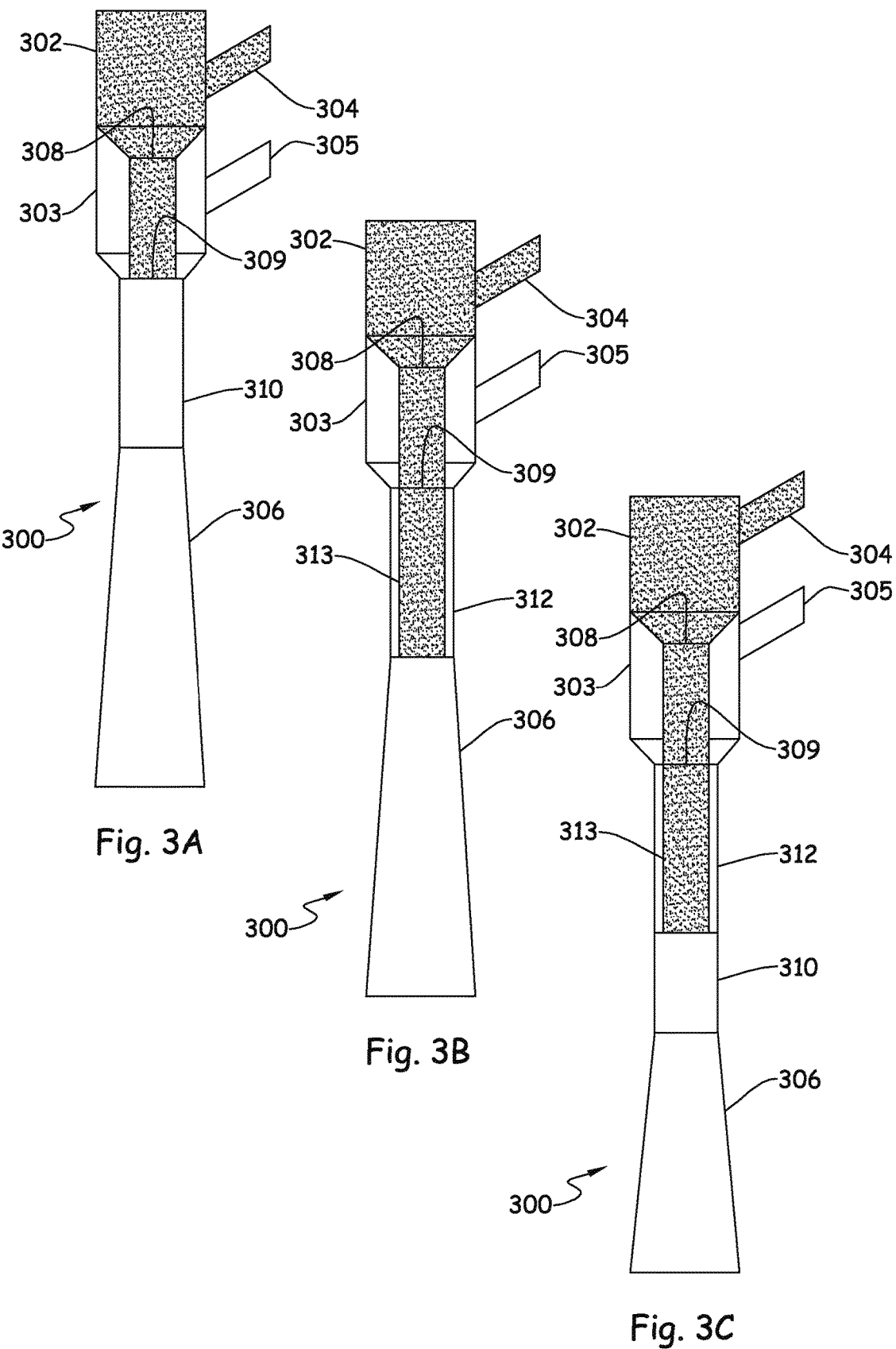
FIG. 3A is a schematic representation (not to scale) of one embodiment of the mixer comprising two inlets/chambers, a mixing zone and an expander zone.
FIG. 3B is a schematic representation (not to scale) of one embodiment of the mixer comprising two inlets/chambers, a flow pattern development zone and an expander zone.
FIG. 3C is a schematic representation (not to scale) of one embodiment of the mixer comprising two inlets/chambers, a flow pattern development zone, a mixing zone and an expander zone.

Additional embodiments of the mixer are shown in FIG. 3. In addition to the features shown in FIG. 2, the embodiment of mixer 300 shown in FIG. 3A incorporates mixing zone 310. The outlet 308 of chamber 302 and outlet 309 of chamber 303 are arranged concentrically, both ending at the inlet of mixing zone 310. Mixing zone 310 is fluidly connected to expander zone 306.

As shown in FIG. 3B, mixer 300 comprises includes flow pattern development zone 312. As with the embodiment shown in FIG. 3A, outlet 308 and outlet 309 are arranged concentrically, with outlet 308 providing the innermost tube of flow pattern development zone 312. Outlet 309, in combination with outlet 308, provides annular space 313. Outlet 308, outlet 309, and annular space 313 each terminate at, and are fluidly connected with, expander zone 306. In this case, mixing occurs in the expander zone. Mixer 300 can accommodate the introduction of one or more reactants via inlet 304, one or more reactants via inlet 305, and any number of additional reactants introduced by, e.g., injection ports (not shown) as may be provided in mixer 300.

In the embodiment shown in FIG. 3C, mixer 300 includes both flow pattern development zone and mixing zone 310. The outlets of chambers 302 and 303 are arranged as shown and described in connection with FIG. 3B. And so, in operation of mixer 300 shown in FIG. 3C, one or more reactants may be injected through inlet 304 and one or more reactants may be provided through inlet 305. The desired flow pattern, as may be encouraged by the chamber inlet angle α and tangential chamber-inlet angle γ, may further develop within flow pattern development zone 312. The reactants would then be mixed within mixing zone 310.

FIG. 4A-4C show additional embodiments of the mixer, comprising three inlets. In the embodiment shown in FIG. 4A, mixer 400 includes three inlets and two chambers, with two inlets 405 and 414 being provided to chamber 403. FIG. 4B shows a further embodiment wherein a third chamber 415 is provided, arranged about the same concentric axis as chambers 402 and 403, but lying within chamber 403. FIG. 4C shows an embodiment of mixer 400 including a third chamber 415, wherein chamber 415 is arranged about the same concentric axis as chambers 402 and 403, and between flow pattern development zone 412 and mixing zone 410. In other embodiments, third chamber 415 could be provided downstream from, and about the same concentric axis as, chambers 402 and 403, but upstream from flow pattern development zone 412. Mixer 400 as shown in FIG. 4A-4C include both flow pattern development zone 412 and mixing zone 410, although this need not be the case, and any of the embodiments of mixer 400 shown in FIG. 4A-4C may be provided only with chambers 402, 403 and 415 and expander zone 406.

In some embodiments, the outlet of the mixer may desirably be operably disposed relative to the reactor that would desirably receive the mixed reactants, i.e., the mixer outlet may be directly coupled to a reactor inlet, or may be coupled to any other conduit capable of fluidly coupling the mixer outlet with the reactor inlet. Any such conduit is desirably configured so as to be substantially the same shape as the fluid flow from the reactor, e.g., to be substantially tubular or conical. Any such conduit will also desirably be placed about the same longitudinal axis as the outlet of the mixer.

Whether directly attached to the reactor, or to a conduit there between, the advantages provided may be realized or enhanced by using certain reactor features and/or dimensions to assist in the design of the mixer. The incorporation of the expander into the present mixer allows an advantageous inlet arrangement to be used, having an inner diameter that more closely approximates the inner diameter of the feedstream source line, while yet having an outlet that more closely approximates the reactor inlet inner diameter.

Table 2, below, provides a correlation between dimensions and features of the mixer with common reactor sizes with which the mixer may advantageously be used, for an exemplary process wherein two reactants are introduced to two inlet/chambers. Table 2 is by no means exhaustive, and those of ordinary skill will be able to extrapolate the dimensions and ranges given to any type of reactor, having any dimensions, and to any type of process.

TABLE 2

| Approximate Reactor ID | 4" | 8' |
|---|---|---|
| Reactor Dimensions | | |
| ID ($D_r$), in | 3.826 | 96 |
| Length, in | 70.87 | 231 |
| Mixer Dimensions | | |
| Chamber/inlet number | 2 | 2 |
| Mixer head ID (inch) | 2 | 28 |
| Inlet 1 ID | (0.1-0.5) | (4-12) |
| Chamber 1 (central) outlet | | |
| ID | 0.25-0.75 | 4-12 |
| Inlet 2 ID | 0.1-0.5 | 4-12 |
| Chamber 2 (outer) outlet | | |
| ID | 0.6-1.4 | 9-27 |
| Flow pattern development zone, Length (in) | 3-9 | 12-48 |
| Mixing zone, Length (in) | 6-18 | 12-72 |
| Expander Zone | | |
| Angle from longitudinal axis | 1-20 | 1-20 |

The mixer can be attached to a reactor with various configurations. In order to provide a desired residence time, a reactor for the production or chlorinated propenes may typically be quite long, and so one or more sections of the reactor and/or mixer may be nonlinear, i.e., one or more zones thereof may comprise bends of 45° or greater, or 90° or greater, or even 135° or greater. In some embodiments, the reactor and/or mixer may comprise multiple bends, and in such embodiments, may even take the form of a serpentine pattern. Incorporating bends into the reactor and/or mixer allows the desired lengths to be utilized for each zone, while yet minimizing the manufacturing footprint required for the reactor and the mixer.

The present mixer/reactor apparatus provides significant advantages when used in connection with chemical processes comprising a limiting reagent for which it was designed, and such processes are also provided. Incorporating the present mixer or mixer/reactor apparatus into such a process can reduce, or even eliminate backmixing that may occur in conventional mixers, so that substantial variances in conversions are not seen. Indeed, processes performed using the present mixer and/or apparatus can be provided with minimized production of secondary products and/or decomposition products such that variances of less than 2%, or even less than 1%, from the desired conversion, are seen. A reactor provided with such mixer described here may be operated at substantially longer run-time and hence allowed larger capacity than otherwise. Selectivity may also be substantially maintained, or is expected to decrease by no more than 2%. Such reactions may also typically include at least one limiting reactant having desired conversions that are far from exhaustion, e.g., conversions of less than 80%, or less than 40%, or even less than 20%.

The efficiencies provided by the present mixers and apparatus can be further leveraged by providing the chlorinated and/or fluorinated propene and higher alkenes produced therein to further downstream processes. For example, 1,1,2,3-tetrachloropropene produced using the described reactors can be processed to provide further downstream products including hydrofluoroolefins, such as, for example, 2,3,3,3-tetrafluoroprop-1-ene (HFO-1234yf) or 1,3,3,3-tetrafluoroprop-1-ene (HFO-1234ze). Improved methods for the production of hydrofluoroolefins, 2,3,3,3-tetrafluoroprop-1-ene (HFO-1234yf) or 1,3,3,3-tetrafluoroprop-1-ene (HFO-1234ze), are thus also provided herein.

The conversion of chlorinated and/or fluorinated propene and higher alkenes to provide hydrofluoroolefins may broadly comprise a single reaction or two or more reactions involving fluorination of a compound of the formula $C(X)_mCCl(Y)_n(C)(X)_m$ to at least one compound of the formula $CF_3CF=CHZ$, where each X, Y and Z is independently H, F, Cl, I or Br, and each m is independently 1, 2 or 3 and n is 0 or 1. A more specific example might involve a multi-step process wherein a feedstock of 1,1,2,3 tetrachloropropene is fluorinated in a catalyzed, gas phase reaction to form a compound such as 2-chloro-3,3,3-tri-fluoropropene. The 2-chloro-2,3,3,3-tetrafluoropropane is then dehydrochlorinated to 2,3,3,3-tetrafluoropropene via a catalyzed, gas phase reaction.

EXAMPLE 1

Figure 5A:
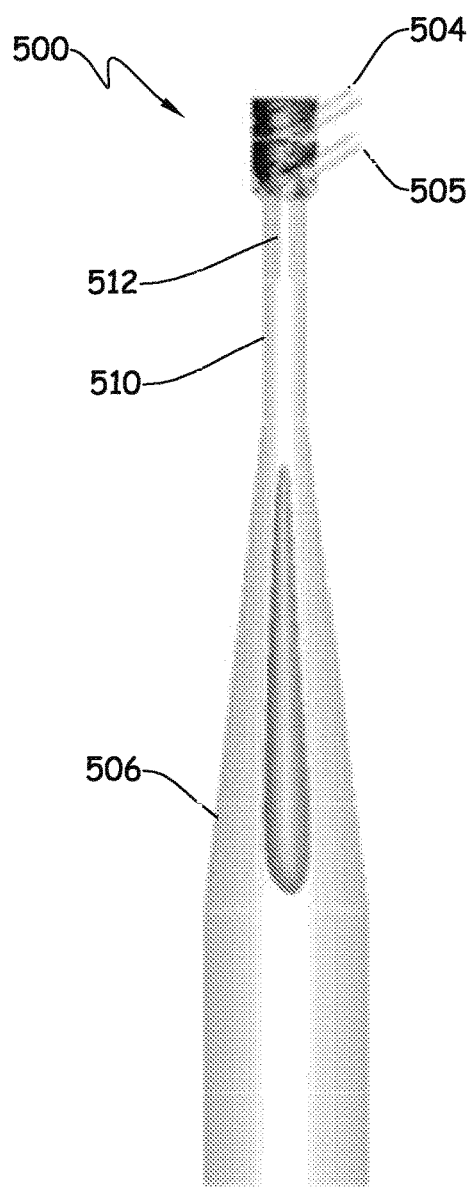
FIG. 5A shows results of a computational fluid dynamic simulation for a mixer according to one embodiment, having two inlets/chambers, a flow pattern development zone, a mixing zone and an expander zone.
Figure 5B:
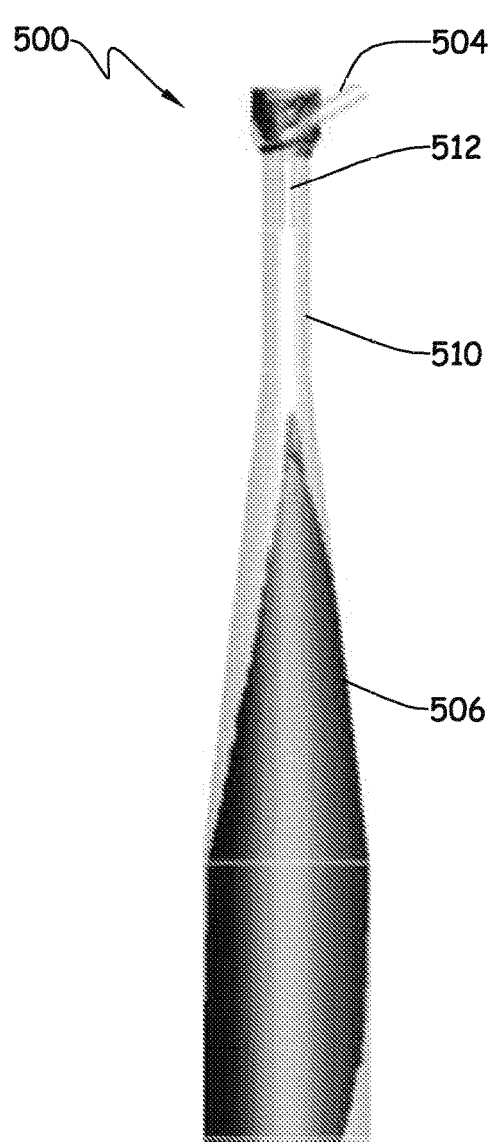
FIG. 5B shows results of a computational fluid dynamic simulation for a mixer according to one embodiment, having one inlet/chamber, a flow pattern development zone, a mixing zone and an expander zone.

FIGS. 5A and 5B shows two mixers designed to provide a swirling flow pattern to the reactants provided thereto. In both embodiments, mixer 500 incorporates angle α of 45°, angle β of 7°, and angle γ of 60°. The flow rate of the reactant provided via inlet 504, methyl chloride, is 215.4 kg/hr, while the flow rates of the reactant mixture provided via inlet 505 in the embodiment of mixer 500 shown in FIG. 5A, carbon tetrachloride and perchloroethylene, are 236.5 kg/hr and 10.2 kg/hr, respectively. In the embodiment of mixer 500 shown in FIG. 5B, the reactant mixture provided via inlet 505 in FIG. 5A is provided via an injection port (not shown) in FIG. 5B upstream of the flow pattern development zone. The inner diameter of the outermost chamber outlet ($D_{co}$), the outermost tube of the flow pattern development zone, and the mixing zone is 1.5". The flow development zone length ($L_{fpd}$) is 8 inches and the mixing zone ($L_m$) is 12 inches.

The results of a computational fluid dynamic simulation are also shown in FIGS. 5A and 5B. More specifically, as shown in FIG. 5A, the embodiment of mixer 500 comprising 2 inlets and chambers results in only the formation of a small area of backmixing, indicated by the shaded area within expander zone 506. Although the backmixing area produced by the embodiment of mixer 500 shown in FIG. 5B is larger, the embodiment of mixer 500 is nonetheless advantageous due to the inclusion of expander zone 506. That is, mixer 500 shown in FIG. 5B is expected to be much less expensive to manufacture than a mixer not comprising an expander zone, i.e., wherein the mixer outlet closely approximates the inner diameter of a reactor inlet.

What is claimed is:

1. A mixer for use in a chemical process comprising;
A first chamber having a first chamber inlet and a first chamber outlet
A second chamber having a second chamber inlet and a second chamber outlet;
A flow pattern development zone comprising a first tube within a second tube wherein the first tube is fluidly connected to the a first chamber outlet and the second tube is fluidly connected to the a second chamber outlet; and
An expander zone having an outer diameter substantially equal to that of the second chamber outlet and/or second tube of the flow pattern development zone and an inner diameter that expands outwardly at an expander angle ($\beta$) of less than 90°;
Wherein the chamber inlet angle ($\alpha$) of at least one of the first or second chamber inlet(s) is less than 90°, the first chamber outlet is arranged concentrically within the second chamber outlet, the flow pattern development zone is upstream of the expander zone and the first tube of the flow pattern development zone ends at an inlet of the expander zone;
wherein the chamber-inlet angle ($\alpha$) is from 30 to 80°;
wherein the angle ($\gamma$) between the chamber inlet and a line tangential to the chamber projected on a cross sectional plane to the chamber intersecting the point where the longitudinal axis of the inlet line meets the chamber's wall is 20° to 60°; and
wherein the mixer further comprising a mixing zone downstream of the flow pattern development zone and upstream of the expander zone, wherein the mixing zone has an outer diameter substantially equal to that of the flow pattern development zone and the first tube of the flow pattern development zone ends at the outlet of the mixing zone.

2. The mixer of claim 1, wherein the expander angle ($\beta$) is less than 20°.

3. The mixer of claim 1, wherein the inner diameter of the at least one of the first or second chambers is at least 1.25 times greater than the inner diameter of its respective chamber inlet.

4. The mixer of claim 1, wherein the inner diameter of at least one of the first or second chamber is greater than the inner diameter of its respective outlet.

5. The mixer of claim 1, wherein an annular space is created by the first and second chamber outlets and the ratio of the cross sectional area of the first chamber outlet to the cross sectional area of the annular space is between 1 and 3.

6. The mixer of claim 1, wherein the length of the flow pattern development zone is at least 0.5 times the diameter of the second chamber outlet.

7. The mixer of claim 1, wherein the inner diameter of the mixing zone is less than or equal to the inner diameter of the second tube of the flow pattern development zone.

8. The mixer of claim 4, wherein the inner chamber of at least one of the first or second chambers is tapered to provide its respective chamber outlet.

9. The mixer of claim 1, wherein the mixing zone comprises a single tube fluidly connected to the outermost chamber outlet and/or outermost tube of the flow pattern development zone, wherein the length of the mixing zone is substantially the same as or greater than the inner diameter of the mixing zone.

10. An apparatus comprising
A reactor having an inner diameter of greater than 0.1 feet and less than 36 feet; and the mixer according to claim 1 having an inlet with an inner diameter of less than the reactor inner diameter.

11. The apparatus of claim 10, wherein the ratio of the inner diameter of the chamber outlet of the mixer to the inner diameter of the reactor is from 2 to 5.

* * * * *